United States Patent [19]
Ong et al.

[11] Patent Number: 5,091,182
[45] Date of Patent: Feb. 25, 1992

[54] DISPENSING UNITS FOR KETOROLAC TOPICAL GEL FORMLATIONS

[75] Inventors: John T. H. Ong, Palo Alto; Jean S. Fujiki, Sunnyvale; Wei-Cheng Liaw, Redwood City, all of Calif.

[73] Assignee: Syntex (U.S.A.) Inc., Palo Alto, Calif.

[21] Appl. No.: 556,938

[22] Filed: Jul. 23, 1990

[51] Int. Cl.⁵ ............................................. A61K 09/00
[52] U.S. Cl. ................................... 424/400; 514/817; 514/886; 514/887; 514/944; 514/947
[58] Field of Search ...................... 424/401, 427, 428; 514/886, 887, 969, 944, 817, 947

[56] References Cited

U.S. PATENT DOCUMENTS

| | | | |
|---|---|---|---|
| 4,089,969 | 5/1978 | Muchowski et al. | 514/416 |
| 4,418,841 | 12/1983 | Eckstein | 222/107 |
| 4,454,151 | 6/1984 | Waterbury | 514/413 |
| 4,540,572 | 9/1985 | Seth | 424/81 |
| 4,551,371 | 11/1985 | Eckstein | 428/36 |
| 4,568,000 | 2/1986 | Middleton | 222/707 |
| 4,659,408 | 4/1987 | Redding | 428/461 |
| 4,764,361 | 8/1988 | Bilski et al. | 424/45 |
| 4,871,767 | 10/1989 | Beckermann et al. | 514/536 |
| 4,919,939 | 4/1990 | Baker | 424/493 |
| 4,943,780 | 7/1990 | Redding | 428/35.9 |
| 4,946,787 | 8/1990 | Eppstein et al. | 435/240.2 |

Primary Examiner—Thurman K. Page
Assistant Examiner—Robert H. Harrison
Attorney, Agent, or Firm—Carol J. Roth; Derek P. Freyberg; Tom M. Moran

[57] ABSTRACT

A dispensing unit for a ketorolac topical gel formulation is disclosed, wherein the dispensing unit comprises a ketorolac topical gel formulation and a gas-impermeable multi-layered container wherein the container is comprised of a polyolefin inner layer and a metal foil outer layer.

12 Claims, No Drawings

DISPENSING UNITS FOR KETOROLAC TOPICAL GEL FORMLATIONS

BACKGROUND OF THE INVENTION

This invention relates to dispensing units for ketorolac topical gel formulations which are comprised of the gel formulation in a gas-impermeable multi-layered container.

Ketorolac and its pharmaceutically acceptable salts are known to be effective in treating inflammation and pain in mammals. See, e.g., U.S. Pat. No. 4,089,969 and U.S. Pat. No. 4,454,151. Dispensing units for ketorolac topical gel formulations require specific packaging specifications in order to maintain chemical stability of the formulation and physical integrity of the container. For example, the use of containers which are constructed of only polyolefins for dispensing units for ketorolac topical gel formulation results in undesirable changes in the formulation due to solvent evaporation. We have discovered that a dispensing unit for ketorolac topical gel formulations which is comprised of a container constructed of a polyolefin inner layer and a metal foil outer layer will maintain the chemical stability of the formulation contained within while at the same time the physical integrity of the container is maintained.

SUMMARY OF THE INVENTION

This invention is a dispensing unit for a ketorolac topical gel formulation, wherein the dispensing unit comprises:
(a) a ketorolac topical gel formulation comprising:
 (i) ketorolac, or a pharmaceutically acceptable salt thereof, in an amount between 0.1% and 5.0% w/w;
 (ii) a lower alkanol in an amount between 30% and 45% w/w;
 (iii) a thickening agent in an amount sufficient to gel said formulation; and
 (iv) water q.s. to 100%; and
(b) a gas-impermeable multi-layered container containing said formulation, which container comprises:
 (i) an inner layer in direct contact with said formulation, which inner layer comprises a polyolefin; and
 (ii) an outer layer comprising a metal foil.

DETAILED DESCRIPTION OF THE INVENTION

Definitions

As used in this specification, unless specified to the contrary, the following terms have the meaning indicated:

"Ketorolac" is ($\pm$)-5-benzoyl-2,3-dihydro-1H-pyrrolizine-1-carboxylic acid (USAN).

The term "polyolefin" refers to a thermoplastic polymer derived from olefins by homopolymerization, e.g., polyethylene (such as low density polyethylene), polypropylene, polybutylene, and the like; or by copolymerization of an olefin with at least one other olefinically unsaturated monomer, such as another olefin, giving copolymers such as ethylene-propylene copolymers, or monomers containing vinyl esters or acrylic acid or ester groups giving copolymers such as ethylene/acrylic acid copolymer (EAA), ethylene/vinyl acetate copolymer (EVA), and the like.

The term "lower alkanol" refers to a saturated aliphatic hydrocarbon that has from one to six carbon atoms and that is substituted by one hydroxy group, e.g., methanol, ethanol, isopropyl alcohol, n-butanol, or t-butyl alcohol.

The term "penetration enhancer" refers to a compound that enhances the penetration through the skin of the active ingredient(s) of a formulation in which the penetration enhancer is contained, e.g., ethanol, propylene glycol, pyrrolidones, dimethyl sulfoxide, dimethylacetamide, dimethylformamide, 1-dodecylazacycloheptan-2-one (Azone®) decylmethyl sulfoxide, oleic acid or diisopropyl adipate. A typical effective amount of a penetration enhancer in a ketorolac topical gel formulation is between about 0.5% and 5.0% w/w.

The term "chelating agent" refers to a compound that complexes metal ions which catalyze the degradation of the active ingredient(s) of a formulation in which the chelating agent is contained, e.g., ethylenediaminetetraacetic acid (EDTA), citric acid, dihydroxyethyl glycine, tartaric acid, tryptophan, and their pharmaceutically acceptable salts, e.g., EDTA disodium salt. An effective amount of a chelating agent in a ketorolac topical gel formulation is between about 0.001% and 0.1% w/w.

The term "antioxidant" refers to a compound that retards deterioration by oxidation of the active ingredient(s) of a formulation in which the antioxidant is contained, e.g., sodium bisulfite, ascorbic acid, butylated hydroxytoluene (BHT) or butylated hydroxyanisole (BHA). An effective amount of an antioxidant of a ketorolac topical gel formulation is between about 0.001% and 0.1% w/w.

The term "thickening agent" refers to a compound that, when added to a liquid or solution, produces a gel. Examples of thickening agents for aqueous or aqueous/alcoholic solutions are carboxymethylcelluloses; hydroxyalkylcelluloses, e.g., hydroxymethylcellulose and hydroxypropylcellulose; carboxyvinyl polymers having a molecular weight of approximately from 1,250,000 to 4,000,000, e.g, carbomer 934, carbomer 940, and carbomer 941; and polyoxypropylene-polyoxyethylene block polymers, e.g., Pluronic® F127. Carbomers are synthetic high molecular weight polymers of acrylic acid cross-linked with allyl ethers of sucrose or pentaerythritol. Pluronics® are polyoxypropylene-polyoxyethylene block polymer available from BASF-Wyandotte. Pluronics® are identified by a letter prefix followed by a two or a three digit number. The letter prefixes L, P and F refer to the physical form of each polymer, i.e., L-liquid, P-paste, and F-flakeable solid. The two and three digit numbers are used to designate the average molecular weight of the polyoxypropylene hydrophobic midsection of the block polymer in comparison with the percent polyoxyethylene in the total molecule.

The term "pharmaceutically acceptable salt" refers to those salts which retain the biological effectiveness and properties of the free bases and which are not biologically or otherwise undesirable. These salts are prepared from either inorganic or organic bases. Salts derived from inorganic bases include, but are not limited to, the sodium, potassium, lithium, ammonium, calcium, magnesium, ferrous, zinc, copper, manganous, aluminum, ferric, manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The term "pH control agent" refers to those organic and inorganic bases and acids which may be added to a formulation of the invention in order to maintain the pH of the formulation within a certain range. For example, tromethamine may be added to a formulation in order to raise the pH; hydrochloric acid, in order to lower it. A desirable pH for a formulation of the invention is from about 3.8 to about 4.6, preferably at about 4.2.

The ketorolac topical gel formulations contained within the dispensing units of the invention are generally prepared by first dissolving ketorolac, or a pharmaceutically acceptable salt thereof, and a chelating agent in purified water to form an aqueous solution. If necessary, a pH control agent, preferably tromethamine, is then added to the aqueous solution in order to maintain the desired pH of the formulation. In a separate vessel, a lower alkanol, preferably isopropyl alcohol; a penetration enhancer, preferably diisopropyl adipate; and an antioxidant, preferably BHT, are then mixed together to form an alcoholic solution. A thickening agent, preferably a carboxyvinyl polymer, e.g., carbomer 940, is then evenly dispersed into this alcoholic solution. The aqueous solution containing ketorolac, or a pharmaceutically acceptable salt thereof, is then added to the alcoholic solution and the resulting mixture is slowly stirred until gelling is complete.

The gas-impermeable multi-layered containers of the dispensing units are constructed of a material comprised of consecutive layers which are firmly adhered to each other to make a unitary structure. Examples of such material are described in U.S. Pat. No. 4,659,408 (American Can Company) and U.S. Pat. No. 4,418,841 (American Can Company). The consecutive layers of the containers are positioned such that only one layer is in direct continuous contact with the formulation contained within. The term "inner layer" therefore refers to that layer of the container which is in direct contact with the formulation contained therein. Such inner layers are comprised of a polyolefin, as defined above.

The term "outer layer" refers to a layer of the container which is outside of the inner layer, as described above. Such outer layer is comprised of a metal foil which prevents the passage of gases or vapors to and from the contained formulation. The outer layer need not be in direct contact with, or adjacent to, the inner layer, i.e., another layer or other layers may be between the inner layer and the outer layer. Such outer layer also need not be the outermost layer of the container, i.e., another layer or other layers may be outside the outer layer. Layers other than the inner layer and the outer layer may be comprised of polyolefins or paper.

The containers, as described above, may be in various shapes and forms, including, but not limited to, tubes and pouches. It is preferred that such containers are capable of being deformed or collapsed by external pressure in order to extrude a formulation contained therein.

The dispensing units of the invention are therefore prepared by filling by conventional methods known to those skilled in the art a gas-impermeable multi-layered container, as described above, with a ketorolac topical gel formulation, as prepared above. The resulting dispensing unit may then be used to topically administer an amount of the formulation contained therein to an animal, preferably a human, in need thereof.

PREFERRED EMBODIMENTS

Dispensing units of the invention are comprised of a ketorolac topical gel formulation, which is comprised of ketorolac, or a pharmaceutically acceptable salt thereof, in an amount between 0.1% and 5.0% w/w; a lower alkanol in an amount between 30% and 45% w/w; a thickening agent in an amount sufficient to gel the formulation; and water q.s. to 100%; and a gas-impermeable multi-layered container containing the formulation, which container is comprised of an inner layer in direct contact with the formulation, which inner layer comprises a polyolefin; and an outer layer comprising a metal foil. Within this group of dispensing units, certain subgroups are preferred.

One preferred subgroup are those dispensing units wherein the lower alkanol is selected from the group consisting of isopropyl alcohol and ethanol, and the thickening agent is selected from the group consisting of a carboxyvinyl polymer and hydroxypropyl cellulose. Within this subgroup a preferred class of dispensing units are those dispensing units wherein the formulation is further comprised of an effective amount of a penetration enhancer; an effective amount of a chelating agent; and an effective amount of an antioxidant. Within this class a preferred subclass of dispensing units are those dispensing units wherein the penetration enhancer is selected from the group consisting of diisopropyl adipate, 1-dodecylazacycloheptan-2-one, and oleic acid; the chelating agent is selected from the group consisting of the disodium salt of EDTA and citric acid; and the antioxidant is selected from the group consisting of BHT and BHA. Within this subclass the most preferred dispensing units are those dispensing units wherein the formulation is comprised of about 1.0% w/w of ketorolac tromethamine; about 35.0% w/w of isopropyl alcohol; about 2.0% w/w of diisopropyl adipate; about 0.01% w/w of the disodium salt of EDTA; about 0.01% w/w of BHT; about 2.5% w/w of carbomer 940; and water q.s.

Another preferred subgroup of dispensing units are those dispensing units wherein the inner layer is an ethylene/acrylic acid co-polymer and the outer layer is aluminum foil. Within this subgroup a preferred class of dispensing units are those units wherein the inner layer is between about 1.0 and 3.2 mils thick and the outer layer is between about 0.7 and 1.5 mils thick. Within this class the more preferred dispensing units are those dispensing units wherein the container is in the shape of a deformable tube. Within this class the most preferred dispensing units are those dispensing units wherein the containers are deformable tubes sold under the tradename Glaminate ® (American Can Company).

Presently, the most preferred dispensing units of the invention are those dispensing units wherein the ketorolac topical gel formulation is comprised of about 1.0% w/w of ketorolac tromethamine, about 2.0% w/w of diisopropyl adipate, about 35.0% w/w of isopropyl alcohol, about 0.01% w/w of the disodium salt of EDTA, about 0.01% w/w of butylated hydroxytoluene, about 2.5% w/w of carbomer 940, and water q.s. to 100%; and the gas-impermeable multi-layered container containing the formulation is comprised of an inner layer of a ethylene/acrylic acid co-polymer of about 1.0 to 3.2 mils thick and an outer layer of aluminum foil of about 0.7 to 1.5 mils thick.

The following example is given to enable those skilled in the art to more clearly understand and to practice the instant invention. It should not be considered as a limitation on the scope of the invention, but merely as being illustrative and representative thereof.

EXAMPLE 1

A. This example illustrates the preparation of a representative dispensing unit for a 1.0% ketorolac topical gel formulation.

| Ingredient | % w/w |
| --- | --- |
| ketorolac tromethamine | 1.0 |
| diisopropyl adipate | 2.0 |
| isopropyl alcohol | 35.0 |
| EDTA disodium salt | 0.01 |
| BHT | 0.01 |
| carbomer 940 | 2.5 |
| tromethamine | 0.18 |
| purified water q.s. to | 100.00 |

The above 1.0% ketorolac topical gel formulation was prepared by dissolving the ketorolac tromethamine, EDTA disodium salt and tromethamine in purified water to form an aqueous solution. (Tromethamine was added to maintain the pH of the formulation at pH 4.2±0.2.) The diisopropyl adipate and butylated hydroxytoluene were then dissolved in the isopropyl alcohol to form an alcoholic solution. Carbomer 940 was then slowly dispersed in this alcoholic solution so as to avoid gelling. After the carbomer 940 was completely dispersed, the aqueous solution containing ketorolac tromethamine was then added to the alcoholic solution. The resulting mixture was then brought up to weight with purified water and, if needed, the pH was adjusted with either tromethamine or hydrochloric acid to maintain the pH of the formulation at 4.2±0.2. The resulting formulation was then slowly stirred at temperatures below 20° C. until gelling of the formulation was complete.

Dispensing units containing the above formulation were prepared by filling Glaminate ® tubes, supplied by American Can Company, with the formulation by conventional methods known to those skilled in the art.

B. In a similar manner, dispensing units for the following 2.0% ketorolac topical gel formulation were prepared:

| Ingredient | % w/w |
| --- | --- |
| ketorolac tromethamine | 2.0 |
| diisopropyl adipate | 2.0 |
| isopropyl alcohol | 35.0 |
| EDTA disodium salt | 0.01 |
| BHT | 0.01 |
| carbomer 940 | 2.5 |
| purified water q.s. to | 100.00 |

C. In a similar manner, dispensing units for ketorolac topical gel formulations containing 0.1% to 5.0% w/w ketorolac tromethamine were prepared.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A dispensing unit for a ketorolac topical gel formulation, wherein said dispensing unit comprises:
   (a) a ketorolac topical gel formulation comprising:
      (i) ketorolac, or a pharmaceutically acceptable salt thereof, in an amount between 0.1% and 5.0% w/w;
      (ii) a lower alkanol in an amount between 30% and 45% w/w;
      (iii) a thickening agent in an amount sufficient to gel said formulation; and
      (iv) water q.s. to 100%; and
   (b) a gas-impermeable multi-layered container containing said formulation, which container consists of consecutive layers which are firmly adhered to each other to make a unitary structure, wherein:
      (i) the inner layer comprises a polyolefin and is in direct contact with said formulation; and
      (ii) an outer layer comprises a metal foil.

2. A dispensing unit of claim 1 wherein said lower alkanol is selected from the group consisting of isopropyl alcohol and ethanol; and said thickening agent is selected from the group consisting of a carboxyvinyl polymer and hydroxypropyl cellulose.

3. A dispensing unit of claim 2 wherein said formulation further comprises:
   (a) an effective amount of a penetration enhancer;
   (b) an effective amount of a chelating agent; and
   (c) an effective amount of an antioxidant.

4. A dispensing unit of claim 3 wherein said penetration enhancer is selected from the group consisting of diisopropyl adipate, 1-dodecylazacycloheptan-2-one, and oleic acid; said chelating agent is selected from the group consisting of the disodium salt of EDTA and citric acid; and said antioxidant is selected from the group consisting of BHT and BHA.

5. A dispensing unit of claim 4 wherein said formulation comprises:
   (a) 1.0% w/w of ketorolac tromethamine;
   (b) 35.0% w/w of isopropyl alcohol;
   (c) 2.0% w/w of diisopropyl adipate;
   (d) 0.01% w/w of EDTA disodium salt;
   (e) 0.01% w/w of BHT;
   (f) 2.5% w/w of a synthetic polymer of approximately 1,250,000 to 4,000,000 molecular weight composed of acrylic acid crosslinked with allyl ethers of sucrose or pentaerythritol; and
   (g) 0.18% w/w of tromethamine; and
   (h) water q.s.

6. A dispensing unit of claim 4 wherein said formulation comprises:
   (a) 2.0% w/w of ketorolac tromethamine;
   (b) 35.0% w/w of isopropyl alcohol;
   (c) 2.0% w/w of diisopropyl adipate;
   (d) 0.01% w/w of EDTA disodium salt;
   (e) 0.01% w/w of BHT;
   (f) 2.5% w/w of a synthetic polymer of approximately 1,250,000 to 4,000,000 molecular weight composed of acrylic acid crosslinked with allyl ethers of sucrose or pentaerythritol; and (g) water q.s.

7. A dispensing unit of claim 1 wherein said inner layer is an ethylenelacrylic acid co-polymer and said outer layer is aluminum foil.

8. A dispensing unit of claim 7 wherein said inner layer is between about 1.0 and 3.2 mils thick and said outer layer is between about 0.7 and 1.5 mils thick.

9. A dispensing unit of claim 8 wherein said container is in the shape of a deformable tube.

10. A dispensing unit of claim 5 wherein said inner layer of said container is an ethylene/acrylic acid co-polymer and said outer layer is aluminum foil.

11. A dispensing unit of claim 10 wherein said inner layer is between about 1.0 and 3.2 mils thick and said outer layer is between about 0.7 and 1.5 mils thick.

12. A dispensing unit of claim 11 wherein said container is in the shape of a deformable tube.

* * * * *